US006780598B1

(12) United States Patent
Kokolus

(10) Patent No.: US 6,780,598 B1
(45) Date of Patent: Aug. 24, 2004

(54) METHOD OF IDENTIFYING AND LOCATING IMMUNOBIOLOGICALLY-ACTIVE LINEAR PEPTIDES

(76) Inventor: William J. Kokolus, 69 Ferndale Ave., Kenmore, NY (US) 14217

( * ) Notice: Subject to any disclaimer, the term of this patent is extended or adjusted under 35 U.S.C. 154(b) by 0 days.

(21) Appl. No.: 09/552,461

(22) Filed: Apr. 18, 2000

Related U.S. Application Data

(63) Continuation-in-part of application No. 09/097,078, filed on Jun. 12, 1998, now Pat. No. 6,070,126.
(60) Provisional application No. 60/049,613, filed on Jun. 13, 1997, and provisional application No. 60/130,230, filed on Apr. 20, 1999.

(51) Int. Cl.$^7$ ................ G01N 33/53; G01N 33/48; A61K 38/00; C07K 1/00
(52) U.S. Cl. ................ 435/7.1; 530/300; 530/350; 530/388.1; 702/19; 702/20
(58) Field of Search ................ 435/7.1; 530/300, 530/350, 388.1; 702/19, 20

(56) References Cited

U.S. PATENT DOCUMENTS

| | | | | |
|---|---|---|---|---|
| 4,554,101 A | * | 11/1985 | Hopp. | 424/185.1 |
| 5,599,677 A | * | 2/1997 | Dowell et al. | |
| 5,807,978 A | * | 9/1998 | Kokolus et al. | |
| 6,070,126 A | * | 5/2000 | Kokolus et al. | |

FOREIGN PATENT DOCUMENTS

| WO | WO 96/40754 | * 12/1996 |
|---|---|---|

OTHER PUBLICATIONS

Hopp, T. Methods in Enzymology (1981) vol. 178, pp. 571–583.*
Van Oss, Molecular Immunology, 1995, vol. 32, No. 3 pp. 199–211.*
Abramowitz, M. Stegun, I., (eds) "Handbook of Mathematical Functions", *National Bureau of Standards Applied Mathematics Series*, # 55, 71–79, 1964.
Atherton et al., "Peptide Synthesis", *Tetrahedron*, 44:843–857, 1988.
Barany et al., Solid–Phase Peptide Synthesis, *The Peptides*, 2: 1–284, 1988.
Fynan et al., "DNA vaccines: Protective immunization by parenteral, mucosal, and gene–gun inoculations", *Proc. Natl. Acad. Sci. USA*, 90:11478–11482, Dec. 1993.
Henttu et al., "cDNA Coding for the Entire Human Prostate Specific Antigen Shows High Homologies to the Human Tissue Kallikrein Genes", *Biochemical and Biophysical Research Communication*, 160:903–910, 1989.
Hopp et al., "Prediction of protein antigenic determinants from amino acid sequences", *Proc. Natl. Acad. Sci. USA*, 78(6):3824–3828, Jun. 1981.
Kytel et al., "A Simple Method for Displaying the Hydropathic Character of a Protein", *J. Mol. Biol.*, 157:105–132, 1982.
Pellequer et al., "Predicting Location of Continuous Epitopes in Proteins from Their Primary Structures", *Methods in Enzymology*, 203:176–201, 1991.
Robinson, HL, "DNA Vaccines", (Abstract) *Seminars in Immunology*, 9(5) 271, Oct. 1997.
Rosenblum et al., "Amino Acid Sequence Analysis, Gene Construction, Cloning, and Expression of Gelonin, a Toxin Derived from *Gelonium multiflorum*", *J. Interferon and Cytokine Research*, 15:547–555, 1995.

* cited by examiner

Primary Examiner—Marjorie Moran
Assistant Examiner—Lori A. Clow
(74) *Attorney, Agent, or Firm*—The Bilicki Law Firm, P.C.

(57) ABSTRACT

The present invention relates to identifying protein epitopes and more particularly to a novel method for identifying, determining the location, optimal length of amino acid residues and immunobiological potency of protein epitopes by fitting a hydrophilicity and/or hydrophobicity plot generated for the amino acid linear sequence of a polypeptide to a mathematically generated continuous curve thereby generating at least one set of potential epitopes which include ranked potential epitopes having a specific number of amino acid residues. The immunobiologically-active linear peptides are deemed the potential epitopes that exhibit the most alternating positioning about an equilibrium position when juxtaposed on the hydrophilicity and/or hydrophobicity plot and their optimal length corresponds to the specific number of amino acid residues in the set of ranked potential epitopes. The amino acid sequence of the protein epitopes of the present invention exhibit a hydrophobic-hydrophilic-hydrophobic motif

4 Claims, 2 Drawing Sheets

METHOD OF IDENTIFYING AND LOCATING IMMUNOBIOLOGICALLY-ACTIVE LINEAR PEPTIDES

CROSS REFERENCE TO RELATED APPLICATION

Figure 1:
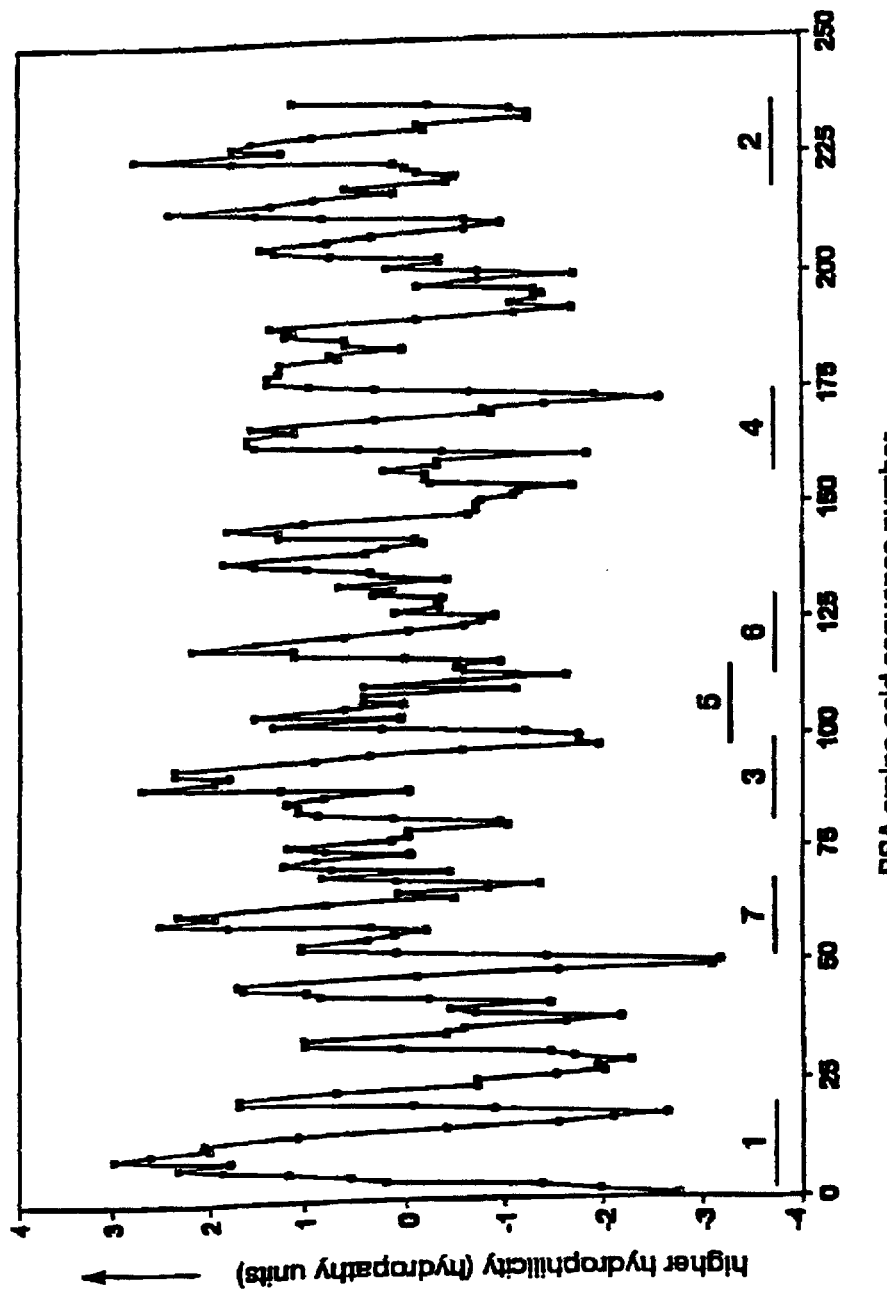

This is a continuation-in-part of Application Ser. No. 09/097,078 filed Jun. 12, 1998 issued May 30, 2000 as U.S. Pat. No. 6,070,126, which claims benefit of U.S. Provisional Application Ser. No. 60/049,613 filed Jun. 13, 1997. This application also claims the benefit of U.S. Provisional Application Ser. No. 60/130,230 filed on Apr. 20, 1999.

TECHNICAL FIELD

The present invention relates to locating protein epitopes and more particularly to novel methods for identifying, determining the location, and the optimal length of immunobiologically active amino acid sequences.

BACKGROUND OF INVENTION

Epitopes or antigenic determinants of a protein antigen represent the sites that are recognized as binding sites by certain immune components such as antibodies or immunocompetent cells. While epitopes are defined only in a functional sense i.e. by their ability to bind to antibodies or immunocompetent cells, it is usually accepted that there is a structural basis for their immunological reactivity.

Epitopes are classified as either being continuous and discontinuous (Atassi and Smith, 1978, *Immunochemisty*, vol 15 p. 609). Discontinuous epitopes are composed of sequences of amino acids throughout an antigen and rely on the tertiary structure or folding of the protein to bring the sequences together and form the epitope. In contrast, continuous epitopes are linear peptide fragments of the antigen that are able to bind to antibodies raised against the intact antigen.

Many antigens have been studied as possible serum markers for different types of cancer because the serum concentration of the specific antigen may be an indication of the cancer stage in an untreated person. As such, it would be very advantageous to develop immunological reagents that react with the antigen, and more specifically, with the epitopes of the protein antigen.

To date, methods using physical-chemical scales have attempted to determine the location of probable peptide epitopes which includes looking at the primary structure, that being the amino acid sequence, secondary structure such as turns, helices, and even the folding of the protein in the tertiary structure. Continuous epitopes are structurally less complicated and therefore may be easier to locate, however, the ability to predict the location, length and potency of the site is limited.

Various methods have been used to identify and predict the location of continuous epitopes in proteins by analyzing certain features of their primary structure. For example, parameters such as hydrophilicity, accessibility, and mobility of short segments of polypeptide chains have been correlated with the location of epitopes (see Pellequer et al. 1991, *Method in Enzyology*, vol 203, p. 176–201).

Hydrophilicity, has been used as the basis for determining protein epitopes by analyzing an amino acid sequence in order to find the point of greatest local hydrophilicity as disclosed in U.S. Pat. No. 4,554, 101. Hopp and Woods (See *Proc. Natl. Acad. Sci. USA*, vol. 78, No. 6, pp. 3824–3828, Jun. 1981) have shown that by assigning each amino acid a relative hydrophilicity numerical value and then averaging local hydrophilicity so that the location of the highest local average hydrophilicity values represent the locations of the continuous epitopes. However, this method does not provide any information as to the optimal length of the continuous epitope.

Likewise, the amino acid sequence of a protein as measured by the Kyte-Doolittle (Kyte and Doolittle, 1982, *J. Mol. Biol.* vol. 72, p. 105) scale, is commonly used to evaluate the hydrophilic and hydrophobic tendencies of polypeptide chains by using a hydropathy scale. Each amino acid in the polypeptide chain is assigned a value reflecting its relative hydrophilicity and hydrophobicity which are averaged across a moving section of the sequence. This method offers a graphic visualization of the hydropathic character of the amino acid chain. It is theorized that by using the hydropathic character of the sequence, interior sequence regions which are usually composed of hydrophobic amino acids can be distinguished from hydrophilic exterior sequence regions. This information offers the ability to evaluate the possible secondary structure. However this model, does not predict the optimal length of the epitope or indicate if the effective size of epitopes is unique for each protein molecule.

Accordingly, what is needed is a simple method to identify immunobiologically-active peptide epitopes, determine their optimal length, and locations of these epitopes within a polypeptide.

SUMMARY OF THE INVENTION

In accordance with this invention there is provided methods for identifying immunobiologically-active linear peptide epitopes of a protein antigen and determining the optimal length of amino acid residues of the epitope.

TERMS

For purposes of this invention, the terms and expressions below, appearing in the specification and claims, are intended to have the following meanings:

"Window" as used herein means the number of amino acid residues in a curve segment.

"Lagging" as used herein means to move across the entire amino acid residues sequence increasing by one (1) in each step.

"Period number" as used herein means the number of amino acids assigned as the period between $-180°$ to $+180°$ in the negative cosine function plot.

"Fit-Correlation Value" as used herein means a numerical value which is indicative of the fit between the hydropathy plot curve and a negative cosine function wherein the value may be positive or negative depending on the fit. The better the fit the more positive the value.

"Epitope" as used herein means the portion of an antigen that binds specifically with the binding site of an antibody or a receptor on a lymphocyte.

"Potential Ho-Hi-Ho epitope" as used herein means an epitope wherein the curve segment of the hydrophilicity plot correlates with the negative cosine function giving a fit-correlation value.

"Potential Ho-Hi-Ho epitope set" as used herein means a set of epitopes having a positive fit-correlation value for a specific period assigned to the negative cosine curve.

"Ho-Hi-Ho theoretical epitopes" as used herein means the epitopes in the potential epitope set that have ranking values that exhibit the most oscillating behavior about an equilibrium position and either converge towards or diverge away from this equilibrium position and are deemed the most immunobiologically-active linear peptides.

"Number Range" as used herein means the numerated amino acid sequence number region of the amino acid sequence having a length equal to a period number, i.e. if the period is 10, then the sequence number ranges could be 1–10, 2–11, 3–12 and so on until (n–(m–1)) where n is equal to the number of amino acid residues in the entire polypeptide and m is the period number.

Immune responses arise as a result of exposure to foreign stimuli. The compound that evokes the response is referred to as antigen or as immunogen. An immunogen is any agent capable of inducing an immune response. In contrast, an antigen is any agent capable of binding specifically to components of the immune response, such as lymphocytes and antibodies. The smallest unit of an antigen that is capable of binding with various immune components, either cells, such as T and B lymphocytes, or antibodies, is called an epitope. Compounds may have one or more epitopes capable of reacting with immune components. The methods of the present inventions provide an in silica methodology for determining the antigen-binding site of an antibody or a receptor on a lymphocyte that has a unique structure that allows a complementary "fit" to some structural aspect of the specific antigen.

Thus understood, a primary object of the present invention is to provide a method for determining immunobiologically-active linear peptide epitopes and their optimal length.

Another object of the present invention is to identify immunobiologically-active linear peptide epitopes without the need for time consuming and expensive testing regimes to determine immunogenic activity, such as in vivo animal testing and/or in vitro assay testing.

A further object of this invention is to determine the immunopotency of an epitope and provide a ranking system delineating between dominant and subdominant epitopes.

A still further object of the invention is to provide monoclonal and polyclonal antibodies highly specific for the peptide epitopes of the present invention which may be utilized in detecting procedures to determine the presence of an antigen in a sample.

Yet another object of the present invention is to provide for synthetic peptides from a protein having the specific amino acid sequence and length determined by the methods herein that may be used in an immunization regime wherein the synthetic peptides are recognized by the body's immune system and induce production of immune components such as antibodies and/or immunocompetent cells, i.e. B and T cells that will react with the peptide or the entire protein.

Another object of the present invention is to provide a method to determine the optimal length of a peptide that binds to antibodies and/or immunocompetent cells.

Still another object is to provide for nucleic acid molecules encoding for the immunobiologically-active linear peptide epitopes having an optimal length found by the methods disclosed herein.

The foregoing objects are achieved by fitting a hydrophilicity and/or hydrophobicity plot generated for the amino acid linear sequence of a polypeptide to a mathematically generated continuous curve which has at least a maximum positive value thereby generating potential epitope sets which include ranked potential epitopes which contain a specific number of amino acid residues. These sets of ranked potential epitopes may be used to determine immunobiologically-active linear peptides by comparison methods, such as a comparison between the sets to determine the set exhibiting the greatest amount of oscillating behavior about an equilibrium position; comparing the ranked potential epitopes with other epitopes generated by propensity scales; comparing with a previously generated plot such as hydrophilicity, accessibility, hydrophobicity and the like; and/or combinations thereof. Preferably, the set of potential epitopes that exhibit the most alternating positioning about an equilibrium position when juxtaposed on the hydrophilicity and/or hydrophobicity plot are deemed the immunobiologically-active epitopes. Their optimal length corresponds to the specific number of amino acid residues in the set of ranked potential epitopes.

This invention relates to an improved method for determining the optimal length of an immunobiologically active epitope that does not require either in vivo animal testing or in vitro immunoassay testing regimes. Unexpectedly it has been discovered by this inventor that an alternating rhythmic pattern in the ranked potential epitopes provides the necessary information to determine the optimal length.

The method for determining the optimal length of an immunobiologically-active linear peptide epitope comprises the following steps:

a) providing a curve characterizing the hydrophilicity and/or hydrophobicity of the linear sequence of amino acid residues of a polypeptide;

b) generating at least one potential epitope set comprising at least one potential epitope by fitting a window of the curve of step (a) to a mathematically generated continuous curve, the continuous curve having repeating values at regular intervals with at least a maximum positive value, the window containing a specific number of amino acid residues and the window is lagged through the curve of step (a);

c) increasing the number of residues in the window after each lagging;

d) determining and ranking potential epitopes for each set by selecting potential epitopes having a positive-fit correlation value determined by fitting curves in step (b) thereby providing a set of ranked potential epitopes for each window of residues used in step (b), the most positive-fit correlation value ranked first in each potential epitope set;

e) examining the positioning of at least the highest ranked potential epitopes of each set relative to the plot of step (a) to determine at least one set of potential epitopes that exhibit alternating positioning about an equilibrium position wherein the ranking values of the potential epitopes converge towards or diverge away from the equilibrium position; and f) designating the potential epitopes of the set having the most alternating ranking values that converge or diverge as the immunologically active epitopes which have an optimal length equating to numeric value of amino acid residues in the potential epitopes.

Preferably, the potential epitopes are generated by fitting a hydrophilicity curve generated by plotting hydropathy values according to the prediction method of Kyte-Doolittle and correlating this curve to a negative cosine function thereby generating Ho-Hi-Ho theoretical epitopes.

The method of the present invention may be used to determine the length of a contiguous amino acid sequence of a polypeptide characterized by a hydrophobic-hydrophilic-hydrophobic motif the method comprising the steps of:

a) assigning an average hydropathy value to each amino acid of the polypeptide;

b) generating a hydrophilicity plot using the average hydropathy value of each amino acid;

c) fitting a curve segment of the hydrophilicity plot to a negative cosine function, wherein a specific period number value of the negative cosine function equates to the number of amino acids in the curve segment, the period number increasing within a predetermined chosen period number range after each sequential lagging through the hydrophilicity plot thereby providing fit-correlation values for each curve segment across the linear sequence when using the specific period number value;

d) generating a potential Ho-Hi-Ho epitope set for each specific period number value within the chosen period number range, wherein each potential Ho-Hi-Ho epitope set contains potential Ho-Hi-Ho epitopes that have a fit-correlation value;

e) ranking each potential Ho-Hi-Ho epitope in the potential Ho-Hi-Ho epitope set according to positive fit-correlation values wherein the epitope having highest positive fit correlation value is ranked number one thereby providing ranked Ho-Hi-Ho potential epitopes for each specific period number value;

f) examining the positioning of at least the highest ranked Ho-Hi-Ho potential epitopes of each set relative to the linear sequence of the generated plot in step (a) to determine at least one set of Ho-Hi-Ho potential epitopes that exhibits alternating positioning about an equilibrium position wherein the ranking values of the Ho-Hi-Ho potential epitopes converge towards or diverge away from the equilibrium position; and g) designating the Ho-Hi-Ho potential epitopes of the set having the most alternating ranking values that converge or diverge as the immunologically active epitopes which have an optimal length equating to numeric value of amino acid residues in the potential epitopes.

The present invention further provides for a Ho-Hi-Ho epitope of contiguous amino acid residues from a polypeptide wherein the Ho-Hi-Ho epitope is defined by a motif of two hydrophobic and one hydrophilic regions arranged in the following manner hydrophobic-hydrophilic-hydrophobic and characterized by an approximated −180° to +180° negative cosine hydrophilicity pattern wherein said Ho-Hi-Ho epitope peptide has an optimal length of amino acid residues from about 3 to about 250. The optimal length of amino acid residues is determined by the methods of the present invention.

Also provided is an antisera specific for a Ho-Hi-Ho epitope of contiguous amino acid residues from a polypeptide wherein the Ho-Hi-Ho epitope is characterized by a hydrophobic-hydrophilic-hydrophobic motif and an approximated −180° to +180° negative cosine hydrophilicity pattern having an optimal length of amino acid residues from about 3 about 250. Additionally, the optimal length may be determined by the method disclosed in the present invention.

There is also provided an antigenic composition comprising a Ho-Hi-Ho epitope of contiguous amino acid residues from a polypeptide wherein the Ho-Hi-Ho epitope is characterized by a hydrophobic-hydrophilic-hydrophobic motif and an approximated −180° to +180° negative cosine hydrophilicity pattern having an optimal length of amino acid residues from about 3 to about 250.

Additionally, the optimal length may be determined by the method disclosed in the present invention.

Still further provided is a diagnostic testing method comprising the steps of:

(i) providing a sample;

(ii) contacting the sample with antisera specific for a Ho-Hi-Ho epitope of contiguous amino acid residues from a polypeptide wherein the Ho-Hi-Ho epitope is characterized by a hydrophobic-hydrophilic-hydrophobic motif having an optimal length of amino acid residues from about 3 to about 250 determined by the methods of the present invention; and (iii) detecting binding of the antisera to a polypeptide in the sample.

Also provided is a diagnostic testing method comprising the steps of:

(i) providing an antisera sample (ii) contacting said antisera sample with at least one Ho-Hi-Ho epitope having an optimal length determined by the present methods; and (iii) detecting the binding said Ho-Hi-Ho epitope to said antisera sample.

Alternatively, the above diagnostic testing method may include a tissue sample which may be contacted with at least one Ho-Hi-Ho epitope.

The present invention also provides for isolated nucleic acid molecules that encode for the Ho-Hi-Ho immunobiologically active epitope having an optimal length determined by the methods of the present invention. The nucleic acid molecule may include; a cDNA molecule comprising the nucleotide sequence of the coding region of the epitope, isolated DNA or RNA molecule or a genetic variant thereof which encodes the immunobiologically active epitope.

BRIEF DESCRIPTION OF THE DRAWINGS

FIG. 1 shows the hydropathy plot for the amino acid sequence of Prostate Specific Antigen (PSA) and the oscillating behavior of the Ho-Hi-Ho theoretical rankings.

FIG. 2 shows the hydropathy plot for the amino acid sequence of Gelonin and the oscillating behavior of the Ho-Hi-Ho theoretical rankings.

DETAILED DESCRIPTION OF THE PREFERRED EMBODIMENTS

The present invention is concerned with providing methods for identifying immunobiologically-active linear epitopes, determining the length of continuous amino acid residues of the identified epitopes and locating their position in a protein antigen.

The method to identify immunobiologically-active linear epitopes, and particularly epitopes characterized by a hydrophobic-hydrophilic-hydrophobic motif, includes generating average propensity values for each amino acid of the protein sequence. These average values may be determined from propensity scales that describe the tendency of each residue to be associated with properties such as accessibility, hydrophilicity, hydrophobicity and/or mobility. Preferably, the average value is determined by a hydrophilicity parameter. These average values may then be plotted. The average values of amino acids can be obtained from any of the methods well known in the art including, but not limited to Kyte-Doolittle tables (Kyte and Doolittle, 1982, J. Mol. Biol., vol 72, p. 105) which are based on solubility of amino acids in water vapors, Hopp-Woods (Hopp and Woods, 1981, Proc. Natl. Acad. Sci., vol. 78, p. 3824) values which are based on the ability of amino acids to bind to a C 18 HPLC column and/or Parker-Hodge (J. M. D. Parker, D. Guo, and R. S. Hodges, 1986, *Biochemistry* 25, 5425) which is based on peptide retention times during high-performance liquid chromatography.

Preferably the Kyte-Doolittle measurement scale is used wherein a hydropathy value is assigned to each natural amino acid based on side chain (i) interior-exterior distribution and (ii) water-vapor transfer free energy as determined by water-vapor partition coefficients. The Kyte-Doolittle hydropathy index values include the following:

Isoleucine (9.5), Valine (4.2), Leucine (3.8), Phenylalanine (2.8), Cysteine/cystine (2.5), Methionine (1.9), Alanine (1.8), Glycine (–0.4), Threonine (–0.7), Tryptophan (–0.9), Serine (–0.8), Tyrosine (–1.3), Proline (–1.6), Histidine (–3.2), Glutamic acid (–3.5), Glutamine (–3.5), Aspartic acid (-3.5), Asparagine (–3.5), Lysine (–3.9), Arginine (–4.5).

NOTE: The above values when used for plotting a curve will provide a hydrophobicity curve. To generate a hydrophilicity curve the sign of the index values must be reversed, e.g., Isoleucine becomes (–9.5).

Figure 2:
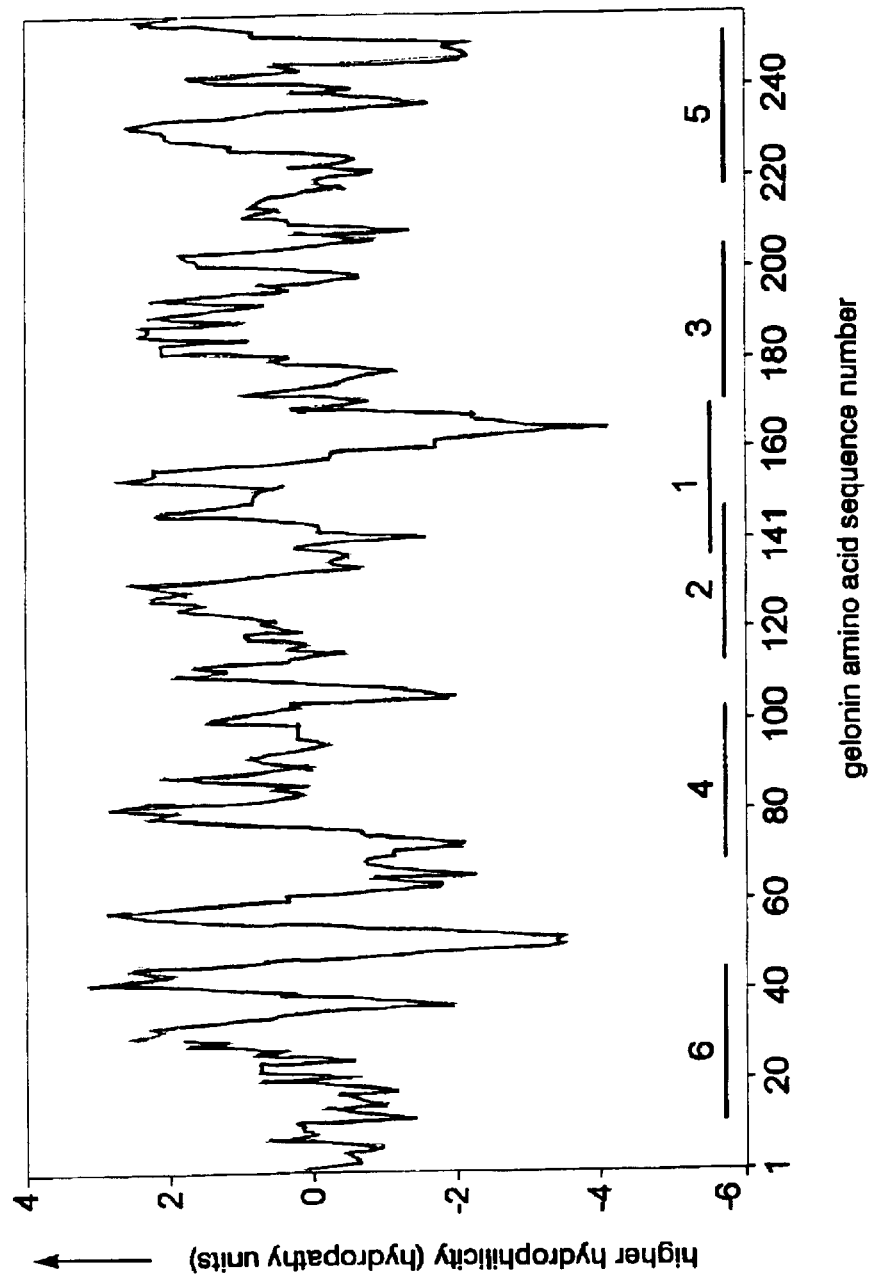

The average hydropathy value of each amino acid is accomplished by averaging the hydropathy values of the amino acid residues within a predetermined segment. The segment may include any number, however, in a preferred embodiment the length of the segment is 5 amino acids. A window average hydropathy value is calculated for each amino acid residue by assigning the average hydropathy value to the amino acid at the center point of each of the moving segments. Average hydropathy values are obtained by shifting the segment by a single amino acid along the entire amino acid sequence of the protein as it advances from the amino to the carboxyl terminus. This is repeated until each amino acid residue is the center point of a segment has been assigned a average hydropathy value. A hydrophilicity an/or hydrophobicity plot of these average hydropathy values is then generated. The plot can be obtained manually, any commercially available or shareware software, or the source code for a custom computer program included in the above-identified reference by Kyte and Doolittle. The hydropathy plot may be generated by the software package "Wisconsin Package v4" commercially available from Genetics Computer Group, Inc., Madison, Wis. FIG. 1 and FIG. 2 are representative examples of a hydropathy plot for prostate specific antigen (PSA) and gelonin, a plant toxin, respectively.

The resulting curve is then fitted to a mathematically generated continuous curve wherein the curve has repeating values at regular intervals with a maximum positive value. The mathematically generated curves may include, but is not limited to trigonometric curves, such as sine, cosine, negative cosine curves, and other curve such as gaussian curves and the like. Preferably, the trigonometric function is a negative cosine function which will identify curve regions representing areas having a hydrophobic-hydrophilic-hydrophobic (Ho-Hi-Ho) pattern. The definition of the negative cosine curve is described according to Abramowitz and Stegun, Eds., HANDBOOK OF MATHEMATICAL FUNCTIONS WITH FORMULAS, GRAPHS AND MATHEMATICAL TABLES, National Bureau of Standards and Applied Mathematics, Series #55, June 1964, p. 71–79. Additionally, the specific definition of the negative cosine curve provided in the Microsoft Fortran Library, version 5.1.

Preferably, successive segments of a protein Kyte-Doolittle hydropathy curve are fitted with the negative cosine curve function using custom software with the source code defined in Appendix A. The custom software determines a fit-correlation value for sequential regions of amino acid residues of the protein. The fit-correlation values are dependent upon the period number of the negative cosine curve function which determines the assigned number of amino acids in each region (window). In other words, the assigned number of amino acids in a curve segment (window) is equivalent to the period number used in the negative cosine function. The period number represents the length of amino acid residues in the hydropathy curve segment that will be analyzed. For each period number specified in the software input, one set (containing of negative cosine function-hydropathy curve region fit-correlation values is generated specific to that period number. The set of fit-correlation values will contain (n–(m–1)) values, where n is the number of amino acids in the protein and m is the period number used in the negative cosine curve function. Specifically, when utilizing the custom software, if $y_l$ is equal to the Kyte-Doolittle hydropathy average value (using a 5-amino acid segment as mentioned above) at the amino acid residue or lag point l, where l=1, . . . , n designates the amino acid residue of an amino acid chain containing n amino acids, then $$\lambda_l = \frac{\sum_{k=0}^{m-1}(y_{l+k} - \overline{y}_l) \cdot (c_k - \overline{c})}{\sqrt{(\sum(y_{l+k} - \overline{y}_l)^2) \cdot (\sum(c_k - \overline{c})^2)}}$$

is the hydropathy curve-negative cosine curve function fit-correlation $\lambda$ at lag point l of period number m where $C_k = -\cos(2\pi k/(m-1))$ is the negative cosine curve function of period number m, and where $$\overline{c} = \sum_{k=0}^{m-1} c_k/m \text{ and } \overline{y}_l = \sum_{k=0}^{m-1} y_{l+k}/m$$

are the respective means.

The fit-correlation process is lagged (shifted) over the entire range of amino acids in the polypeptide by increasing the value of l by one (1) until the value (n–(m–1)) is reached. Subsequently, the period number m of the negative cosine curve function is increased by one (1) in order to generate the next potential Ho-Hi-Ho epitope set. The numerical value for m may be any number greater than 2 extending to the number of amino acid residues in the polypeptide, and preferably, between 3 and 50 thereby creating 48 potential Ho-Hi-Ho epitope sets. Each potential epitope set varies slightly in location as the negative cosine function period number used to generate each set is changed; accordingly, the fit-correlation values vary slightly. By changing the period number of the applied negative cosine function, as one would change the aperture of a camera lens, the mathematical perspective of the negative cosine function curve-fit algorithm is altered. This enables the algorithm to detect sequential amino acid hydrophobic-hydrophilic-hydrophobic patterns of a particular length not readily distinguished visually.

Listed in the output of the specifically designed software are the amino acid sequence number ranges that project a hydropathy curve segment having a fit correlation with the negative cosine curve function and are considered the potential Ho-Hi-Ho epitopes. A positive-fit correlation value indicates the potential presence of a immunobiologically-active linear epitope in the corresponding amino acid sequence number range, i.e. a hydrophobic-hydrophilic-hydrophobic sequence with dominant (high positive-fit correlation) or subdominant (low positive-fit correlation)

immunobiological epitope activity. For each period number m, a set of fit-correlation values is generated. For example, if period number m of the negative cosine curve function is chosen from 3 to 50 then there will be 48 different potential Ho-Hi-Ho epitope sets wherein each set represent a hydropathy curve-negative cosine curve function fit analysis for the entire protein antigen. Each one of these sets has different amino acid sequence number ranges because the period number is changed for each set. For example, the amino acid number ranges for a period number (m) of 10 may include amino acid residues in the number ranges 1–10, 2–11, 3–12, 4–13, and the average hydropathy value for each amino acid in the curve segment (period number range) is inputted into the software program until l is equal to (n−(m−1)). Also, the output will give a fit correlation value for each one of the number ranges such as, 1–10, 2–11, 3–12. More specifically, when using a protein antigen which has 237 amino acid residues in the sequence, l will increase by one until number range 228–237 is inputted into the program. A period number (m) of 11 will include amino acid numbers from 1–11, 2–12, 3–13, 4–14 until l is equal to 227 and number range 227–237 is reached. A set of fit-correlation values from each period number m spans the entire protein antigen and provides a potential Ho-Hi-Ho epitope set.

In each one of the potential Ho-Hi-Ho epitope sets the potential epitopes are ranked according to the magnitude of the positive-fit correlation values. The epitope with the highest fit-correlation value is assigned the number one (1) ranking in each set. This is repeated for each of the sets, that is for each set generated by one of the 48 period numbers utilized by the negative cosine fitting custom software in the range from 3 to 50. The number of amino acid residues in the ranked Ho-Hi-Ho potential epitopes corresponds to the period number m used in the negative cosine function which generated the original potential Ho-Hi-Ho epitope set.

To determine the optimal length of the imnmunobiologically-active epitope and the position of the continuous epitope in a polypeptide, it has been discovered that a recurrent pattern provides the necessary information. Specifically, the ranked potential epitopes for each set are superimposed on the hydrophilicity plot so that the sequence of amino acid residues in the potential epitopes are juxtaposed on the plot to correspond to the linear sequence of the polypeptide as shown in FIGS. 1 and 2.

Each of the generated sets of ranked Ho-Hi-Ho potential epitopes are plotted on the generated hydrophilicity curve thereby providing a plurality of different plots, each one representing a different period number m. Each of the different plots are reviewed to determine which of the plots exhibit an alternating rhythmicity wherein the highest rankings of the potential epitopes oscillate about an equilibrium position and either converge towards or diverge away from this centralized position with the concomitant increasing of the rankings.

This oscillating of the ranking values of the positioned potential epitopes about an equilibrium position may be exhibited in several different plots but the set of potential epitopes having the greatest number of epitopes that exhibit the oscillating behavior provides information for the optimal length. The period number m that was used to generate the set of potential epitopes is consider the optimal number of amino acid residues in an immunobiologically active epitope.

Additionally, it has been found that if more than one plot, having a different period number m, exhibit the same oscillating rhythmicity, then the plot generated by m having the highest fit-correlation values between the hydrophilicity curve and the negative cosine function is considered the potential set having the most immunobiologically-active epitopes and their optimal length is determined by the number of amino acid residues in the ranked potential epitopes.

The disclosed method of generating a plurality of potential epitope sets (for a polypeptide) by fitting a hydrophilicity curve to the curve generated by a negative cosine function may be used with other data to determine and/or verify the optimal length. For instance, the ranked potential epitopes for each set, having a specific length of amino acid residues and a Ho-Hi-Ho motif may be compared or correlated with other ranked epitopes (for the polypeptide in question found) by well known propensity scales that are based on accessibility, hydrophilicity, flexibility, and the like. Along this line, statistical methods may be used to determine the highest correlation coefficient between the rankings of potential epitopes and epitopes found by propensity scales. Likewise, the potential epitope sets may be fitted or juxtaposed on other generated plots including hydrophobicity, The method of the present invention can be used to select immunobiologically-active linear peptide epitopes from a variety of polypeptides once the amino acid sequence of the polypeptide is determined. Any method know in the art which can determine the amino acid sequence of a protein may be used in the present invention. A preferred method is briefly explained. The first step in the sequence determination of a protein is to cleave the polypeptide chain into smaller peptides and then separate homogeneous samples of these peptides. Trypsin is especially useful for this initial cleavage, because of its specificity for lysine and arginine residues. A polypeptide chain containing five such residues, for example, will be cleaved by trypsin into six shorter peptides. The shorter peptides are separated and analyzed. The amino acid sequence of the isolated peptides is then determined by the sequential cleavage of amino acids from the carboxyl-terminal and amino-terminal ends of each peptide. This can be accomplished by the use of exopeptidases which are specific for the amino-or carboxyl-terminal ends of the peptide chain, or by chemical methods. Carboxypeptidase successively cleaves amino acids from the carboxyl-terminal end of the peptide and it is possible to determine the sequence of the amino acids by following the time course for the release of the amino acids. The most useful chemical method for the analysis of peptide sequences is the reaction of N-terminal amino acids with phenylisothiocyanate. This reaction removes amino acids sequentially from the N-terminal end of the chain as their phenylthiohydantoin (PTH) derivatives. In the first step of the reaction, isothiocyanate undergoes nucleophilic attack by the terminal amino group of the peptide to give a substituted thiourea. This step is carried out in dilute base. Upon treatment with a weak acid, the terminal amino group of the thiourea attacks the peptide bond of the terminal amino acid to give the phenylthiohydantoin derivative of the original N-terminal amino acid. This amino acid may be identified by chromatography and by comparing with standard phenylthiohydantoin derivatives of known amino acids. Cleavage of the peptide bond gives a new N-terminal amino acid that may be identified by repetition of the whole process.

Additionally, the method of the present invention may be used to select Ho-Hi-Ho epitopes from cancer cells, viral, microbial, and other molecules of basic and clinical research interest including, but not limited to examples provided below:

Lymphokines and Interferons: IL-1, IL-2, IL-3, IL-4, IL-S, IL-6, IL-7, IL-8, IL-9, IL-10, IL-11, IL-12, IFN-α, IFN-β, IFN-γ.

Cluster Differentiation Antigens and MHC Antigens: CD2, CD3, CD4, CD5, CD8, CD11a, CD11b, CD11c, CD16, CD18, CD21, CD28, CD32, CD34, CD35, CD40, CD44, CD45, CD54, CD56, K2, K1, Pβ, Oα, Mα, Mβ2, Mβ1, LMP1, TAP2, LMP7, TAP1, Oβ, IAβ, IAα, IEβ, IEβ2, IEα, CYP21, C4B, CYP21P, C4A, Bf, C2, HSP, G7a/b, TNF-α, TNF-β, D, L, Qa, Tla, COL11A2, DPβ2, DPα2, DPβ1, DPα1, DNα, DMα, DMβ, LMP2, TAPi1, LMP7, DOβ, DQβ2, DQα2, DQβ3, DQβ1, DQα1, DRβ, DRα, HSP-70, HLA-B, HLA-C, HLA-X, HLA-E, HLA-J, HLA-A, HLA-H, HLA-G, HLA-F.

Hormones and Growth Factors:
nerve growth factor, somatotropin, somatomedins, parathormone, FSH, LK, EGF, TSH, THS-releasing factor, HGH, GRHR, PDGF, IGF-I, IGF-II, TGF-β, GM-CSF, M-CSF, G-CSF1, erythropoietin.

Tumor Markers and Tumor Suppressors: β-HCG, 4-N-acetylgalactosaminyltransferase, GM2, GD2, GD3, MAGE-1, MAGE-2, MAGE-3, MUC-1, MUC-2, MUC-3, MUC4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMel17, tyrosinase related proteins 1and 2, p97, p53, RB, APC, DCC, NF-1, NF-2, WT-1, MEN-I, MEN-II, BRCA1, VHL, FCC and MCC.

Oncogenes:
ras, myc, neu, raf, erb, src, fms, jun, trk ret, gsp, hst, bcl and abil.

Complement Cascade Proteins and Receptors: C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, C5a receptor.

Viral Antigens:
HIV (gag, pol, qp41, gp120, vif, tat, rev, nef, vpr, vpu, vpx), HSV (ribonucleotide reductase, α-TIF, ICP4, ICP8, ICP35, LAT-related proteins, gB, gC, gD, gE, gH, gI, gJ), influenza (hemagluttinin, neuraminidase, PB1, PB2, PA, NP, $M_1$, $M_2$, $NS_1$, $NS_2$), papillomaviruses (E1, E2, E3, E4, E5a, E5b, E6, E7, E8, L1, L2) adenovirus (E1A, E1B, E2, E3, E4, E5, L1, L2, L3, L4, L5), Epstein-Barr Virus (EBNA), Hepatitis B Virus ($gp27^s$, $gp36^S$, $gp42^s$, $p22^c$, pol, x). Nuclear Matrix Proteins.

The Ho-Hi-Ho epitopes of the present invention can be used in diagnostic tests, such as immunoassays, to detect viruses, microbes and malignant cells. Immunoassays, in their most simple direct sense, are binding assays. Immunoassays can detect the presence of a protein as well as determine the concentration of said protein. Certain preferred immunoassays are various types of enzyme linked immunoabsorbent assays, radioimmunoassays, immunofluorescence and surface plasmon resonance. Immunohistochemical detection using tissue sections is also particularly useful. However, it should be appreciated that detection methods are not limited to such techniques, and Western blotting, dot blotting, FACS analyses, and the like may be used.

After identifying the Ho-Hi-Ho epitopes and determining the optimal length of amino acid residue sequence, peptides can be synthesized that correspond to the exact amino acid sequence and length of residues. In turn, polyclonal antibodies or monoclonal antibodies can be generated specific for a peptide.

Briefly, monoclonal antibodies are produced by immunizing animals, such as rats or mice with the peptide antigen of choice. Once the animals are making a good antibody response the spleens or lymph node cells are removed and a cell suspension prepared. These cells are fused with a myeloma cell line by the addition of polyethylene glycol (PEG) which promotes membrane fusion. Only a small proportion of the cells fuse successfully. The fusion mixture is then set up in a culture with medium containing "HAT". HAT is a mixture of Hypoxanthine, Arninopterin and Thymidine. Aminopterin is a powerful toxin which blocks a metabolic pathway. This pathway can be bypassed if the cell is provided with the intermediate metabolites hypoxanthine and thymidine. Thus, spleen cells can grow in HAT medium, but the myeloma cells die in HAT medium because they have a metabolic defect and cannot use the bypass pathway. When the culture is set up in the HAT medium it contains spleen cells, myeloma cells and fused cells. The spleen cells die in culture naturally after 1–2 weeks and the myeloma cells are killed by the HAT medium. Only fused cells survive because they have the immortality of the myeloma cells and the metabolic bypass of the spleen cells. Some of the fused cells will have the antibody producing capacity of spleen cells. The wells containing growing cells are tested for production of the desired antibody (often by RIA or ELISA) and, if positive, the cultures are cloned, that is, plated out so that only one cell is in each well. This process produces a clone of cells derived from a single progenitor, which is both immortal and produces monoclonal antibody. These highly specific, monoclonal antibodies may be used as reagents for numerous applications ranging from specific diagnostic tests to "magic bullets" in immunotherapy of different types of cancer. In immunotherapy, various drugs or toxins may be conjugated to the monoclonal antibodies and delivered to the tumor cells against which the antibodies are specific.

The Ho-Hi-Ho epitopes of the present invention can also be used in prophylactic or therapeutic vaccines to elicit immune responses. Vaccines produced by microorganism such as yeast, through recombinant DNA technology provide another area that may be benefitted by the present invention. The DNA that codes for a Ho-Hi-Ho epitope can be spliced into the DNA of yeast, which, in turn can produce copies of the peptide. In this regard, production of vaccines against hepatitis B may provide greater quantities of a safer vaccine than the vaccine prepared from blood plasma of humans.

Synthetic vaccine can be prepared by chemically synthesizing a chain of amino acids corresponding to the sequence of amino acids of the Ho-Hi-Ho epitopes. The amino acid chain containing the Ho-Hi-Ho epitopes is disposed on a physiologically acceptable carrier and diluted with an acceptable medium. The synthetic vaccines may contain one or a plurality of Ho-Hi-Ho. epitopes of at least one antigen. Vaccines are contemplated for the following antigens, including, but not limited to Hepatitis B surface antigen histocompatibility antigens, influenza hemagglutinin, fowl plague virus hemagglutinin and rag weed allergens Ra3 and Ra5. Also, vaccines are contemplated for the antigens of the following viruses including, but not limited to vaccinia, Epstein Barr virus, polio, rubella, cytomegalovirus, small pox, herpes, simplex types I and II, yellow fever, and many others.

Antigen compositions are contemplated by the present invention which include antibodies specific for peptides with a hydrophobic-hydrophilic-hydrophobic motif having a length of amino acid residues determined by the method of the present invention and which may be administered in the form of injectable, pharmaceutical compositions. A typical composition for such a purpose comprises a pharmaceutically acceptable carrier. For instance, the composition may contain about 10 mg of human serum albumin and from about 20 to 200 micrograms of the labeled monoclonal antibody or fragment thereof per milliliter of phosphate buffer containing NaCl. Other pharmaceutically acceptable carriers include aqueous solution, non-toxic excipients, including salts, preservative, buffers and the like. Examples of non-aqueous solvents are propylene glycol, polyethylene glycol, vegetable oil and injectable organic esters such as ethyloleate. Aqueous carrier include water, alcoholic/aqueous solutions, saline solutions, parenteral vehicles such as sodium chloride, Ringer's dextrose, etc. Intravenous vehicles include fluid and nutrient replenishers. The pH and exact concentration of the various components in the pharmaceutical composition are adjusted according to routine skills in the art.

It is further contemplated that a chain of nucleotides specific to code for a preferred Ho-HI-Ho epitope may be used for immunization compositions. Recently, immunization techniques in which DNA constructs are introduced directly into mammalian tissue in vivo have been developed. Known as DNA vaccines, they use eukaryotic expression vectors to produce immunizing proteins in the vaccinated host. Methods of delivery include intramuscular and intradermal saline injections of DNA or gene gun bombardment of skin with DNA-coated gold beads. Mechanistically, gene gun-delivered DNA initiates responses by transfected or antigen-bearing epidermal Langerhans cells that move in lymph from bombarded skin to the draining lymph nodes. Following intramuscular injections, the functional DNA appears to move as free DNA through blood to the spleen where professional antigen presenting cells initiate responses. These methods are described inter alia in Robinson, *Sources in Immunology*, 9(5): 271–283, (1997 October) and Fynan et al,*Proc. Natl. Acad. Sci. USA*, 90:11478–11482 (1993) and incorporated herein by reference.

In another embodiment of this invention, the method can be used to test the potential antigenicity of a peptide antigen prior to being used to generate bulk antisera for vaccines. The Ho-Hi-Ho epitope of a test antigen can be compared to its standard Ho-Hi-Ho epitope (obtained when the antigen was known to generate efficacious vaccine). Any deviations from the standard values may indicate alteration or denaturation of the antigen. This is also applicable not just for peptide antigens but for any protein. Specifically, if the m-value is determined by the methods of the present invention for a protein, then this value can be used as a comparative value used to determine if a protein used for immunization is viable. For instance, if a protein is used to immunize a subject and the anti-protein antisera does not correctly describe the determined m-value then the protein may have been denatured before the immunization. This knowledge may cause the re-immunize a subject to ensure a sufficient and correct immunological response to the protein.

In yet another embodiment of the invention, the method can be used to determine Ho-Hi-Ho epitopes involved in enzyme-substrate interaction, in protein-protein interaction, protein-nucleic acid interactions, protein-lipid interactions, protein-carbohydrate interactions and the like.

The methods of the present invention may also be used to alter the immunogenicity of a Ho-Hi-Ho epitope, once it has been determined by the methods of the present invention, by altering the amino acid composition therein. Specifically, certain amino acids within the Ho-Hi-Ho epitope may be replaced thereby either increasing or decreasing the fit between the negative cosine curve and generated hydrophilicity curve. By altering the immunogenicity of the epitope, affinity for the epitope binding site by either an antibody or receptor on a lymphocyte can be increased or decreased.

The following examples using prostate specific antigen as a polypeptide having immnuobiologically active linear epitopes will help to illustrate the present invention.

EXAMPLE 1

Hydropathy Plots for PSA and Gelonin

To generate a hydrophilicity plot for prostate specific antigen (PSA), the hydropathy values according to the method of Kyte and Doolittle, were assigned to each amino acid residue. The sign of each value was changed from positive to negative or vice versa dependent upon the original sign. (See Hentuu and Vihko, 1989, *Biochem. Biophys. Res. Comm*, vol. 160, p. 903–910 for the amino acid sequence of the protein). The window average hydropathy values were then plotted for the entire amino acid sequence of PSA. The plot was generated with the software package "The Wisconsin Package v4" commercially available from Genetics computer Group, Inc., Madison, Wis. and shown in FIG. 2. Likewise, a similar plot was generated for Gelonin and shown in FIG. 3. (For sequence, see Rosenblum et al, 1995, J. Interferon-Cytokine Res. vol. 15, p. 547).

EXAMPLE 2

Determination of Hydrophobic-Hydrophilic-Hydrophobic Regions

The negative cosine curve function of a specific period number was fitted with custom software using the source code disclosed in Appendix A to successive segments of the PSA and gelonin Kyte-Doolittle hydropathy curve. Each point along the hydropathy curve obtained in Example 1 was fitted to a negative cosine curve function from −180° to +180°. The period number of the negative cosine curve function was changed from 8 to 40 producing a series of 33 potential Ho-Hi-Ho epitope sets. A fit-correlation value was obtained for each lag point l along the amino acid sequence in each chosen period number m. Number ranges having a positive-fit correlation value represented hydrophobic-hydrophilic-hydrophobic regions in the amino acid sequences and these sequences are deemed ranked theoretical epitopes. The period number m of the negative cosine curve function represented the size of the hydrophobic-hydrophilic-hydrophobic regions, that being, the number of amino acids in the Ho-Hi-Ho epitopes.

EXAMPLE 3

Oscillating Behavior of Ranked Potential Epitope

The Ho-Hi-Ho potential epitopes in each set were determined and ranked according to the positivity of the correlation between the hydrophilicity curve and a curve generated by the negative cosine function wherein the period numbers m=8–40 were used.

The ranked potential epitopes for each set were juxtaposed on the hydrophilicity plot so that the sequence of amino acid residues in the ranked theoretical epitopes corresponded to the linear sequence of the polypeptides of PSA and Gelonin. Thus understood, the amino acid sequence of each ranked Ho-Hi-Ho potential epitope had a specific location corresponding to the placement of the same amino acid sequence found in the polypeptide.

Each of the 33 sets of potential epitopes for PSA and gelonin, which contained the ranked Ho-Hi-Ho potential epitopes, were plotted on the generated hydrophilicity curve thereby providing 33 different plots for each polypeptide. It was discovered in reviewing the plots that the rankings of the potential epitopes were either randomly positioned on the respective plots or the rankings alternated or oscillated about an equilibrium position. This equilibrium position was not necessarily in the center of the linear sequence of the polypeptide. Specifically, in PSA (FIG. 1) the plot which contained the ranked potential epitopes generated when m=19 showed an alternating rhythmicity wherein the highest rankings (1–6) of the positioned Ho-Hi-Ho potential epitopes alternated about a centralized position and converged towards this region. Likewise in FIG. 2 for gelonin it is evident that the highest rankings (1–6) of the potential epitopes exhibit an alternating rhythmicity and diverge from a centralized region between the potential epitopes when the theoretical epitopes were generated using m=31.

Results: It was determined that the immunobiologically-active epitopes are those ranked Ho-Hi-Ho potential epitopes that exhibit the most oscillating behavior about an equilibrium position that either converges to or diverges away from this position. The number of amino acid residues in these ranked potential epitopes was assigned to be the optimal length of the immunobiologically-active epitope. It may be concluded from this example that several amino acid regions in PSA and gelonin adhered strongly to the hydrophobic-hydrophilic-hydrophobic amino acid hydropathy pattern of the protein Ho-Hi-Ho theoretical epitope. This local rhythmic hydropathy pattern enables a protein-specific number of amino acids in the region to act as an immunobiologically active epitope. The epitope length indicated by the optimal negative cosine function period number is specific for PSA (19 amino acids) and for gelonin (31 amino acids). It is theorized that Ho-Hi-Ho theoretical epitopes and their specific length are biochemical entities inherent in a protein. Also, the primary amino acid sequence thus plays a vital role in determining the location, length and immunobiological potency of protein Ho-Hi-Ho theoretical epitopes.

APPENDIX A

FORTRAN PROGRAM FOR FITTING HYDROPATHY PLOT TO NEGATIVE COSINE FUNCTION

```
      program lagfcn
      parameter (mseq1=1000,mlen=50)
      dimension a(mlen),b(mseq1),c(mseq1,mlen)
      character*30 fileout, fileb, filedat
      character*80 forseq
      character*1 seq(mseq1),target
      logical first,last
      mseq=1000
   10 write(*,'("Lag Function Program -- Enter output file")')
      read(*,1) fileout
    1 format (a30)
      write(*,'("Enter min length to max length")')
   11 read(*,*) istart, istop
      if (istop.gt.mlen) then
          Write(*,'("Sequence Length Greater than",i5)') mlen
          Write(*,'("Try again or enter -1 -1 to stop")')
          go to 11
      else
          if (istop.lt.1) go to 999
      end if
      write(*,'("Enter the sequence filename")')
      read(*,1) fileb
      write (*,'("Enter the output data filename")')
      read(*,1) filedat
      open(unit=1,file=fileb,status='OLD')
      inunit=1
      open(unit=7,file=fileout,status='UNKNOWN')
      open(unit=8,file=filedat,status='UNKNOWN')
      write(*,'("Enter length of sequence to be lagged on")')
      read(*,*) lenseq
      write(*,'("Enter target")')
      read(*,3) target
    3 format(80a1)
      write(*,'("Enter 1 to input sequence")')
      write(*,'("Enter 2 to input sequence and hydro.")')
      read(*,*) inptype
      if (inptype .eq. 2) go to 500
      call kytedoo(length,lenseq,seq,b,mseq,inunit)
      go to 60
  500 write(*,'("Enter sequence format -- seq,b")')
      read(*,2) forseq
    2 format (a80)
      do 50 1=1,lenseq
      do 25 i=istart,istop
   25 c(l,i)=0.0
   50 read(1,forseq,end=55) seq(1),b(1)
      length=lenseq
      go to 60
```

APPENDIX A-continued

FORTRAN PROGRAM FOR FITTING HYDROPATHY PLOT TO NEGATIVE COSINE FUNCTION

```
   55  write(7,54) 1
       write(*,54) 1
   54  format('Sequence terminated short of end',i5)
       length=1
   60  continue
       write(7,51) (b(1),1=1,lenseq)
   51  format('Sequence to lag over fcn')(1x,8f9.5))
       write(*,'("Current function is -cosine**power")')
       write(*,'("Enter the integer power, sign and cycles")')
       read(*,*) npower,sig,cycles
       do 100 i=istart,istop
       write(7,52) i
       write(*,52) i
   52  format('Lag',i5,'Calculate Function')
       call fcn(a,i,npower,sig,cycles)
       write(7,53)
       write(*,53)
       write(7, *) (a(j),j=1,i)
c      write(*, *) (a(j),j=1,i)
   53  format('Calculate lags')
       len=lenseq-i
       call lag1(lenseq,b,i,a,c(1,i),1,len)
c      kmin=i/4
c      kmax=3*(i+1)/4
       first=.true.
       last=.false.
       if(cycles.gt.1.) then
           kmin=1
           kmax=i
       else
       do 65 j=1,i
           if (first .and. -sign(1,sig)*a(j).gt.0.) then
               first=.false.
               kmin=j
           end if
           if (.not. first .and. .not. last .and.
     $         -sign(1,sig)*a(j).lt.0.) then
               last=.true.
               kmax=j-1
               go to 70
           end if
   65  continue
       end if
   70  continue
       call p3seq(istart,c(1,i),len,seq,lenseq,target,noin,noout,1,
     $       kmin,kmax)
       ntottar=0
       do 80 l=1,lenseq
           if (seq(1).eq. target) ntottar=ntottar+1
   80  continue
       ntot=noin+noout
       write(7,99) i,noin,noout,ntot,ntottar,kmin,kmax
       write(8,99) i,noin,noout,ntot,ntottar,kmin,kmax
       write(*,99) i,noin,noout,ntot,ntottar,kmin,kmax
   99  format(7i5)
  100  continue
       do 110 l=1,lenseq
       write(8,101) 1,(c(l,i),i=istart,istop)
  101  format(i5,10f8.5)
  110  continue
  999  stop
       end
       subroutine p3seq(n,c,len,seq,lseq,target,ni,no,inc,
     $         kl,ku)
       character*1 seq(lseq),target
       dimension c(len),f(3),x(3)
       data f/ -1,2,-1 /
       ni=0
       no=0
       x(1)=0.
       write(*,1)
       write(7,1)
```

APPENDIX A-continued

FORTRAN PROGRAM FOR FITTING HYDROPATHY PLOT TO NEGATIVE COSINE FUNCTION

```
    1   format(10x,'Position',2x,'Correlation','Target Seq',10x,'X')
        do 100 i=1,len
            x(2)=c(i)
            x(3)=c(i+inc)
            s=0.
            do 20 j=1,3
                s=s+f(j)*x(j)
   20       continue
c           if(s .gt. 0) then
            if(x(2)-x(1) .gt.0.).and.(x(2)-x(3) .gt.0.)) then
                kmin=i+kl
                kmax=i+ku
                do 40 k=kmin,kmax
                    if (seq(k).eq. target) go to 45
   40           continue
                no=no+1
                k=(kmin+kmax)/2
                go to 47
   45           ni=ni+1
   47           write(*,46) i,c(i),target,seq(k),k,x
                write(7,46) i,c(i),target,seq(k),k,x
   46           format(10x,i5,2x,f10.5,2(2x,a1),i4,2x,3f10.5)
   50       continue
            end if
            if (i-inc .ge. 0) x(1)=c(i-inc+1)
  100   continue
        return
        end
        subroutine fcn(a,n,npower,sig,cycles)
        dimension a(n)
        pi=3.14159
        twopi=pi*2
        ratio=cycles*twopi/float(n-1)
        do 100 i=1,n
        arg=(i-1)*ratio
        dat=cos(arg)
  100   a(i)=sig*sign(1.,dat)*(abs(dat))**npower
        return
        end
        SUBROUTINE LAG1(LA,A,LB,B,C,LSTART,LSTOP)
C
C
C       THIS ROUTINE CALCULATES A SAMPLE CROSS-CORRELATION OF THE RECORD
C           A OVER THE RECORD B WITH LAGS BETWEEN LSTART AND LSTOP AND
C           STORES THE RESULT IN C
C       **** CAUTION ***** THERE IS NO CHECK FOR A ZERO RECORD
C
        DIMENSION A(LA),B(LB),C(LA)
        DO 50 J=LSTART,LSTOP
        U=0.0
        SUMA=0.0
        SUMB=0.0
        SA=0.0
        SB=0.0
        IF(LB-(LA-J+1)) 10,10,20
   10   N=LB
        GO TO 30
   20   N=LA-J+1
        IF(N.GT.0) GO TO 30
        DO 25 I=J,LSTOP
   25   C(I)=-2.
        RETURN
   30   EN=N
        DO 40 I=1,N
        IJ=I+J-1
        SUMA=SUMA+A(IJ)
        SUMB=SUMB+B(I)
        SA=SA+A(IJ)*A(IJ)
        SB=SB+B(I)*B(I)
   40   U=U+A(IJ)*B(I)
        SUMA=SUMA/EN
        SUMB=SUMB/EN
        SA=SA-SUMA*SUMA*EN
        SB=SB-SUMB*SUMB*EN
```

APPENDIX A-continued

FORTRAN PROGRAM FOR FITTING HYDROPATHY PLOT TO NEGATIVE COSINE FUNCTION

```
 50   C(J)=(U-EN*SUMA*SUMB)/SQRT(SA*SB)
      RETURN
      END
      subroutine kytedoo (length,lenseq,seq,b,mseq1,inunit)
      dimension b(mseq1), weights(21)
      character*1 seq(mseq1), name(20), buff(80), seqname(80)
      character*1 gt,ast,blank
      data name/'G', 'Q', 'S', 'Y', 'A', 'K', 'T', 'W',
  2              'V', 'H', 'D', 'C', 'L', 'R', 'E', 'M',
  3              'I', 'F', 'N', 'P'/
      data gt/'>'/, ast/'*'/, blank/' '/
      data weights /-0.4,-3.5,-0.8,-1.3, 1.8,-3.9,-0.7,-0.9,
  2                  4.2,-3.2,-3.5, 2.5, 3.8,-4.5,-3.5, 1.9
  3                  4.5, 2.8,-3.5,-1.6, 0.0/
      numprot=20
      l=0
 10   read(inunit,1,end=1000) buff
  1   format(80a1)
      do 100 i=1,80
      if (buff(i) .eq. gt) go to 50
      if (buff(i) .eq. ast) go to 110
      if (buff(i) .eq. blank) go to 10
      l=l+1
      if (l .gt. mseq1) go to 1000
      seq(l) = buff(i)
      write(*,*) 1,mseq1,i,seq(l),buff(i)
      go to 100
 50   write(*,'("Sequence Name",80a1)') (buff(j),j=i+1,80)
      k=0
      do 60 j=i+1,80
      k=k+1
 60   seqname(k)=buff(j)
      l=0
      go to 10
100   continue
      go to 10
110   length=l
      write(*,2) (seq(j),j=1,length)
  2   format(1x,80a1)
      write(*,'("Enter Kyte-Doolittle number to average")')
      read(*,*) l
      l2=l/2
      lstart=l2+1
      lstop=length-l2
      do 120 i=1,l2
      b(i)=0
120   b(length-i+1)=0
      do 200 i=lstart,lstop
      b(i)=0
      do 150 j=i-l2,i+l2
         do 130 k=1,numprot
         if (seq(j) .eq. name(k)) go to 140
130      continue
      write(*,131) j,seq(j)
131   format('At', i4, 1x,a1, 'not recognized – weight =0')
      k=21
140   b(i)=b(i)+weights(k)
150   continue
200   continue
      write(*,'("Kyte-Doolittle calculation complete")')
      write(7,'("Kyte-Doolittle calculation complete")')
      write(7,201) (seq(i),b(i),i=1,length)
201   format(8(1x,a1,1x,f6.3))
      return
1000  write(*,1001) 1,mseq1
1001  format('Unexpected end of file or'/
  2          'sequence length',i5,'too long for buffer',i5)
      return
      end
```

What is claimed is:

1. A method for detecting a protein of known sequence comprises the steps of:
  determining an optimal immunobiologically active linear epitope of said protein of known sequence, wherein said protein is comprised of a plurality of amino acids, and wherein said optimal immunobiologically active linear epitope is characterized by a hydrophobic-hydrophilic-hydrophobic (Ho-Hi-Ho) motif determined by a method comprising the steps of:
    assigning an average hydropathy value to each of said plurality of amino acids of said protein of known sequence;
    generating a hydrophilicity plot using said average hydropathy value;
    fitting each of a plurality of curve segments of said hydrophilicity plot to one of a plurality of a negative cosine functions, wherein one of a plurality of a specific period number values of said plurality of negative cosine functions equates to a particular number of amino acids in one of said plurality of curve segments, said period number value increasing within a predetermined chosen period number range after a sequential lagging of each of said plurality of curve segments through said hydrophilicity plot thereby providing a fit-correlation value for each of said plurality of curve segments across said known sequence of said protein when using one of said plurality of said period number values;
  generating a potential Ho-Hi-Ho epitope set for each of said plurality of specific period number values within said chosen period number range wherein said potential Ho-Hi-Ho epitope set contains at least one potential Ho-Hi-Ho epitope in which said fit-correlation value is positive;
  ranking each of said potential Ho-Hi-Ho epitopes of said potential Ho-Hi-Ho epitope set and assigning a ranking value to each of said potential Ho-Hi-Ho epitopes according to said fit-correlation value wherein said potential Ho-Hi-Ho epitope with a highest positive fit-correlation value is ranked number one, thereby providing a ranked Ho-Hi-Ho potential epitope for each of said plurality of specific period number values;
  examining said ranking value of each of said potential Ho-Hi-Ho epitopes relative to said hydrophilicity plot to determine at least one potential Ho-Hi-Ho epitope set that exhibits alternating positioning around an equilibrium position, wherein a plurality of said ranking values of said potential Ho-Hi-Ho epitopes converge towards or diverge away from said equilibrium position; and
    designating each of said Ho-Hi-Ho epitopes, wherein said ranking values exhibit a most alternating ranking value that converges or diverges from said equilibrium position as said optimal immunobiologically active epitope wherein a numeric value of amino acid in said potential Ho-Hi-Ho epitopes is equal to one of said plutality of specific period number values of said negative cosine function;
  synthesizing at least one peptide corresponding to at least one of said optimal immunobiologically active linear epitopes;
  creating at least one antisera against said synthesized peptides corresponding to at least one of said optimal immunobiologically active linear epitopes;
  providing a sample to be analyzed for said protein of known sequence;
  contacting said sample with said at least one antisera; and
  detecting a binding of said antisera to said protein of said sample, thereby indicating presence of said protein in said sample.

2. The method of claim 1, wherein said protein is selected from a group consisting of IL-1, IL-2, IL-3, IL-4, IL-5, IL-6, IL-7, IL-8, IL-9, IL-10, IL-11, IL-12, IFN-α, IFN-βIFN-65, CD2, CD3, CD4, CD5, CD8, CD11A, CD11b, CD11c, CD16, CD18, CD21, CD28, CD32, CD34, CD35, CD40, CD44, CD45, CD54, CD56, K2, K1, Pβ, Oα, Mα, Mβ2, Mβ1, LMP1, TAP2 LMP7, TAP1, Oβ, IAβ, IAα, IEβ, IEβ2, IEα, CYP21, C4B, CYP21P, C4A, BF, C2, HSP, G7a/b, TNF-α, TNF-β, D,L, Qa, Tla, COL11A2, DPβ2, DPα2, DPβ1, DP 1, DN 2, DQ 3, DQ 1, DQ 1, DR, DR, HSP-70, HLA-B, HLA-C, HLA-X, HLA-E, HLA-J, HLA-A, HLA-H, HLA-G, HLA-E NGF, somtotropin, somatomedins, parathormone, FSH, LH, HEGF, TSH, THS-releasing factor, HGH, GRHR, PDGF, IGF-I, IGF-II, TGF-, GM-CSF, M-CSF, G-CSF1, erythropoietin -ICG, 4-N-acetylgalactosaminyltransferase, GM2, GD2, GD3, MAGE-1, MAGE-2, MAGE-3, MUC-1, MUC-2, MUC-3, MUC-4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMEL 17, tyrosine related proteins 1and 2, p97, p53, RB, APC, DCC, NF-1, NF-2, WT-1, MEN-I, MEN-II, BRCA1, VHL, FCC, MCC, ras, myc, neu, raf, erb, src, fms, jun, trk, ret, gsp, hst, bcl, abil, C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, HIV (gag, pol, qp41, gp120, vif, tat, rev, nef, vpr, vpu, vpx), HSV (ribonucleotide reductase, -TIF, ICP4, ICP8, ICP35, LAT-related proteins, gB, gC, gD, gE, gI, gJ), influenza (hemagluttinin, neuraminidase, PB1, PB2, PA, NP, $M_1$, $M_2$, $NS_1$, $NS_2$), papillomaviruses (E1, E2, E3, E4, E5a, E5b, E6, E7, E8, L1, L2), adenovirus (E1A, E1B, E2, E3, E4, E5, L1, L2, L3, L4, L5), Epstein-Barr Virus (EBNA), Hepatitis B Virus ($gp27^s$, $gp36^s$, $gp42^s$, $p22^c$, pol, x) and nuclear matrix proteins.

3. A method for detecting a protein of known sequence comprising the steps of:
  determining an optimal immunobiologically active linear peptide epitope of said protein, wherein said protein is comprised of a plurality of amino acids, wherein said optimal immunobiologically active linear peptide epitope is characterized by
    fitting a hydrophilicity/hydrophobicity plot generated for said protein of known sequence to a mathematically generated continuous curve thereby generating at least one potential Ho-Hi-Ho epitope which includes at least one ranked potential Ho-Hi-Ho epitope, wherein one of a plurality of a numeric value is assigned to each of said potential Ho-Hi-Ho epitope set corresponding to a fit-correlation value of said hydrophilicity/hydrophobicity plot to said mathematically generated continuous curve, wherein said mathematically generated continuous curve has a period equal to a number of amino acids corresponding to the length of said potential Ho-Hi-Ho epitope, said mathematically generated curve having a maximum positive value;
    positioning said at least one ranked potential Ho-Hi-Ho epitope on said hydrophilicity/hydrophobicity plot to determine an oscillating behavior of said plurality of numeric values of said at least one ranked potential Ho-Hi-Ho epitope and deeming each of said plurality of ranked potential Ho-Hi-Ho epitope that exhibit a most alternating either convergent or divergent positioning about an equilibrium position when juxtaposed on said hydrophilicity/hydrophobicity plot as said optimal immunobiologically active linear peptide epitope, wherein said optimal immunobiologically active linear peptide epitope and its optimal length corresponds to a number of amino acids in the a set of ranked potential Ho-Hi-Ho epitope;

synthesizing at least one peptide corresponding to a least one of said optimal immunobiologically active linear epitopes;

creating at least one antisera against said synthesized peptides corresponding to at least one of said optimal immunobiologically active linear epitopes;

providing a sample to be analyzed for said protein of known sequence;

contacting said sample with said at least one antisera; and detecting a binding of said antisera to said protein of said sample, thereby indicating presence of said protein in said sample.

4. The method of claim 3, wherein said protein is selected from a group consisting of IL-1, IL-2, IL-3, IL-4, IL-5, IL-6, IL-7, IL-8, IL-9, IL-10, IL-11, IL-12, IFN-α, IFN-β, IFN65, CD2, CD3, CD4, CD5, CD8, CD11A, CD11b, CD11c, CD16, CD18, CD21, CD28, CD32, CD34, CD35, CD40, CD44, CD45, CD54, CD56, K2, K1, Pβ, Oα, Mα, Mβ2, Mβ1, LMP1, TAP2, LMP7, TAP1, Oβ, IAβ, IAα, IEβ, IEβ2, Eα, CYP21, C4B, CYP21P, C4A, BF, C2, HSP, G7a/b, TNF-α, TNF-β, D, L, Qa, TIa, COL11A2, DPβ2, DPα2, DPβ1, DN 2, DQ 3, DQ 1, DQ 1, DR , DR , HSP-70, HLA-B, HLA-C, HLA-X, HLA-E, HLA-J, HLA-A, HLA-H, HLA-G, HLA-F, NGF, somatotropin, somatomedins, parathormone, FSII, LH, EGF, TSH, THS-releasing factor, HGH, GRHR, PDGF, IGF-I, IGF-II, TGF-, GM-CSF, M-CSF, G-CSFI, erythropoietin, -IICG, 4-N-acetylgalactosaminyltransferase, GM2, GD2, GD3, MAGE-1, MAGE-2, MAGE-3, MUC-1, MUC-2, MUC-3, MUC4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMEL17, tyrosine related proteins 1and 2, p97, p53, RB, APC WT-1, MEN-I, MEN-II, BRCA1, VHL, FCC and MCC ras, myc, neu, raf, erb, src, fms jun, trk ret, gsp, hst, bcl and abil, C1q, C1r, C1s, C4, C2, Factor D, Factor B, properdin, C3, C5, C6, C7, C8, C9, CUnh, Factor H, C4b-binding protein, DAF, membrane cofactor protein, anaphylatoxin inactivator S protein, HRF, MIRL, CR1, CR2, CR3, CR4, C3a/C4a receptor, HIV (gag, pol, qp41, gp120, vif, tat, rev, nef, vpr, vpu, vpx), HSV (ribonucleotide reductase, -TIF, ICP4, ICP8, ICP35, LAT-related proteins, gB, gC, gD, gE, gI, gJ), influenza (hemagluttinin, neuraminidase, PB1, PB2, PA, NP, $M_1$, $M_2$, NS $_1$, $NS_2$), papillomaviruses (E1E2, E3, E4, E5a, E5b, E6, E7, E8, L1, L2) adenovirus (E1A, E1B, E2E3, E4, E5, L1, L2, L3, L4, L5), Epstein-Barr Virus (EBNA), Hepatitis B Virus ($gp27^s$, $gp36^s$, $gp42^s$, $p22^c$, pol, x) nuclear matrix proteins.

* * * * *